United States Patent [19]

Garrett et al.

[11] 4,170,224
[45] Oct. 9, 1979

[54] BODY FLUID MEASURING DEVICE

[75] Inventors: Scott T. Garrett, Highland Park; William L. Rudzena, Fox Lake; Thurman S. Jess, Mundelein, all of Ill.

[73] Assignee: Baxter Travenol Laboratories, Inc., Deerfield, Ill.

[21] Appl. No.: 844,680

[22] Filed: Oct. 25, 1977

[51] Int. Cl.² ............................................. A61B 5/02
[52] U.S. Cl. ..................................... 128/748; 128/674
[58] Field of Search .......... 128/2 F, 2 G, 2 R, 2.05 D

[56] References Cited

U.S. PATENT DOCUMENTS

| | | | |
|---|---|---|---|
| 3,435,819 | 4/1969 | Reynolds et al. | 128/2.05 D |
| 3,636,942 | 1/1972 | Nye | 128/2.05 D |
| 3,730,168 | 5/1973 | McWhorter | 128/2 F |
| 3,933,439 | 1/1976 | McDonald | 128/2 F |

Primary Examiner—William E. Kamm
Attorney, Agent, or Firm—Paul C. Flattery; John P. Kirby, Jr.; Gary W. McFarron

[57] ABSTRACT

In apparatus for indicating and regulating the pressure of a selected body fluid, an elongated indicator tube with pressure limiting opening means is carried in a vented chamber and mountable in a substantially vertical position. A drip platform circumscribes the indicator tube at a position below the pressure limiting opening means to channel fluid overflowing through the opening means away from the indicator tube and to permit the fluid to flow into the bottom of the chamber free of contact with the side of the indicator tube. The chamber in which the indicator tube is mounted may be defined by an elongated hollow member closed at each end with one-piece end closures which include integral attachment fingers for mounting the chamber and indicator tube in a vertical position.

4 Claims, 4 Drawing Figures

U.S. Patent  Oct. 9, 1979  4,170,224
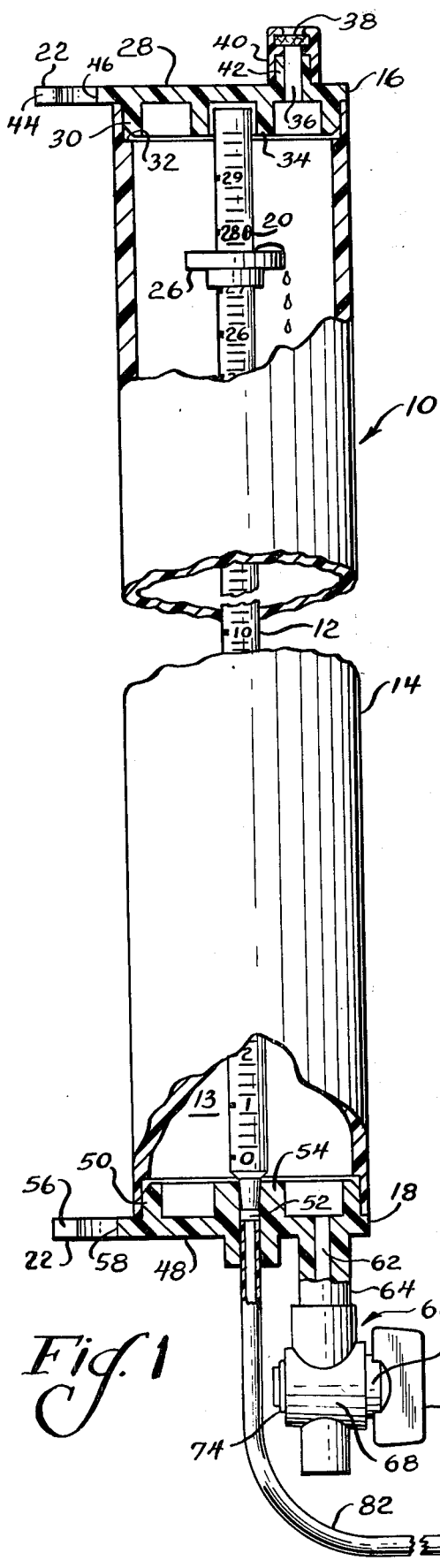
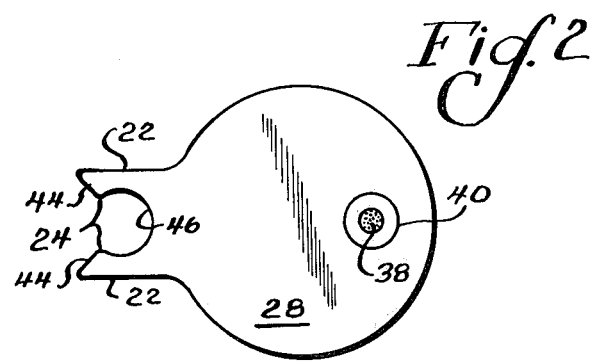
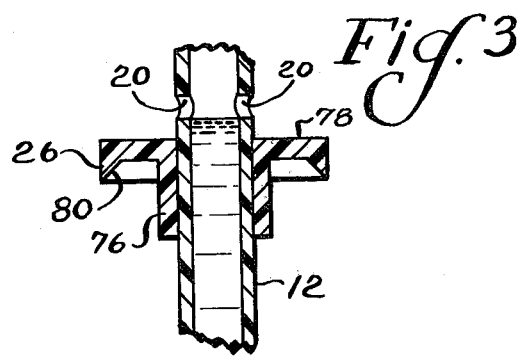
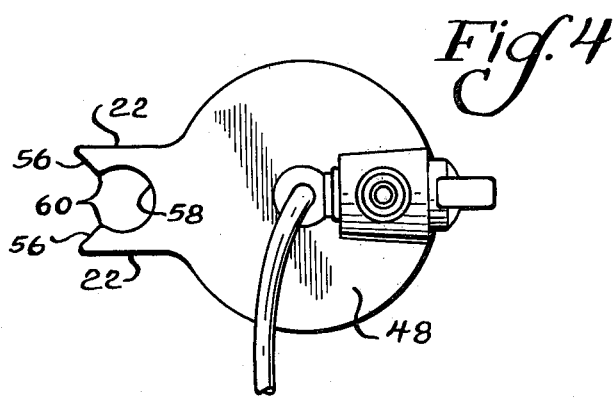
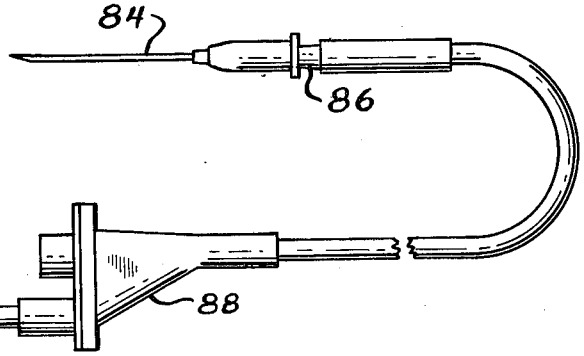

BODY FLUID MEASURING DEVICE

The present invention relates to improvements in medical apparatus for indicating and regulating the pressure of a selected body fluid. More particularly, the present invention is directed to improvements in apparatus which employ a manometer-type pressure indicator tube with opening means in the manometer tube to provide an overflow upper limit to fluid pressure.

In apparatus employing a manometer-type tube for indicating and monitoring body fluid pressure, the manometer tube is usually mounted in a substantially vertical position so that the height of fluid in the tube is an indication of the pressure of the body fluid. In addition, the manometer tube may include openings at a selected position to provide an upper limit on the pressure that the body fluid may attain. When the fluid is of sufficient pressure to reach the openings, it overflows from the tube, usually running down the tube into the bottom of the chamber, where it collects. Thus, a continuous stream of liquid may exist between the openings in the manometer tube and the bottom of the chamber. The problem with this, however, is that fluid collecting in the bottom of the chamber may provide a medium for the growth of bacteria or other harmful microorganisms, which could then migrate directly up the fluid path along the manometer, into the overflow openings and through the fluid column into the patient. Such a fluid measuring device is shown in U.S. patent application Ser. No. 841,253, filed Oct. 11, 1977.

In addition to eliminating a direct fluid path for the migration of microorganisms, it is also desirable that the pressure indicator and regulator be provided as a one-piece, pre-sterilized unit which is easy to mount in a vertical position near the patient and doesn't require additional or costly mounting apparatus not usually found in a hospital.

Accordingly, it is an object of the present invention to provide a fluid pressure indicator and regulator which may be manufactured as a compact unit and which may be simply and quickly mounted in a vertical position. It is a further object of the present invention to provide means in a body fluid pressure indicator and regulator for isolating any fluid which may collect in the collection chamber from the pressure limiting openings in the manometer so that a direct fluid path is not provided for the migration of bacteria or other microorganisms.

These and other objects are met by the present invention by providing an elongated fluid chamber which is closed at each end by one-piece caps, each cap having integral snap-on retaining fingers for mounting the chamber in a vertical position on a standard I.V. pole or stand. A manometer tube is employed in the chamber and has opening means at a selected position for proving an upper limit to the body fluid pressure. A drip platform or umbrella is provided around the manometer tube just below the openings so that fluid escaping through the openings runs across the platform and drips or flows from the edge of the platform into the bottom of a chamber, free of any contact with the surface of the manometer tube. With this construction, there is no direct fluid path to the column of body fluid in the manometer for the migration of bacteria or other harmful microorganisms.

These and other objects of the present invention are set forth in the following detailed description and the attached drawings, of which:

FIG. 1 is an elevational view, partially in section and partially cut away, of a body fluid pressure indicator and regulator constructed in accordance with the present invention.

FIG. 2 is a top view of the fluid pressure indicator and regulator of FIG. 1, showing the top cap with integral retaining fingers.

FIG. 3 is a sectional view of a manometer tube with a drip platform surrounding the tube just below pressure limiting openings in the tube, which embodies the present invention.

FIG. 4 is a bottom view of the fluid pressure indicator and regulator of FIG. 1.

The present invention is generally embodied in a disposable pressure indicator and regulator, generally at 10, which employs a manometer tube 12 in an elongated chamber 13 formed by a cylindrical barrel 14 closed at upper and lower ends by the end caps 16 and 18, respectively. The manometer may include openings 20 at a selected position for providing upper pressure limits to the body fluid. Fluid reaching the openings is discharged into the space between the manometer and the surrounding barrel.

In accordance with the present invention, each end cap has integrally formed attachment means such as a pair of parallel extending fingers 22 with facing detents 24 for snap-on attachment to an upright standard, such as an I.V. pole, for mounting the chamber and manometer in a substantially vertical position. Also in accordance with the present invention, overflow control means, preferably in the form of a drip platform 26, is provided around the manometer, just below the openings 20, and extends outwardly therefrom for conveying fluid escaping from the openings away from the manometer tube.

Turning now to a move detailed description of the attached drawings, which show the preferred embodiments of the present invention for purposes of illustration and not limitation, the barrel 14 is of generally hollow cylindrical shape and is preferably fully transparent. It may be constructed of glass, but clear, rigid, non-toxic plastic, such as polyvinylchloride or polystyrene, is preferred, because it is strong, easy to work with and of relatively low cost.

The barrel is closed at the top by the upper end cap 16, which is of integral, one-piece construction. The end cap includes a flat circular plate portion 28 with a peripheral depending flange 30 of appropriate size to fit snugly against the inside surface of the bell. As shown in the drawing, the inside surface of the barrel end may be machined to form a seat 32 for the cap flange. The cap further includes a center circular depending flange 34 which forms a center guide slot for receiving the upper end of the manometer tube 12. A vent port 36 is also provided in the cap for venting the inside of the barrel.

To filter out harmful microorganisms from any air entering the barrel, a microporous hydrophobic filter membrane 38 having an average pore size less than about 0.5 microns is mounted over the vent port 36. The filter membrane is held in a flexible overring 40 which is fitted over an upstanding cylindrical wall portion 42 of the vent port 34. As best seen at the top of FIG. 1, the overring has an internal should on which the microporous membrane rests. The end of the overring is then heat-formed or swaged inwardly to grip and seal the peripheral edge of the microporous membrane. The preferred fitting between the overring and the upstanding cylindrical wall of the vent port is a tight slip-fit, but the overring may also be more securely fixed, as by a solvent or adhesive.

For mounting the barrel 14 in a substantially vertical position, the upper end cap 16 has a pair of parallel outwardly extending fingers 22, which are molded as an integral part of the cap. The fingers are generally parallel and lie substantially in the same plane as the circular plate portion 26 of the end cap. The inside, facing surface of each finger is generally defined by a tapered end surface 44 which is intersected by a generally circularly curved surface 46, which is sized to correspond to the most popular size I.V. pole now in use, about 0.75 inches in diameter. The detents 24 are formed at the intersections between the curved surface 46 and the tapered end surfaces 44. The distance between the detents is less than diameter of the curved surface, but the plastic cap is sufficently flexible and resilient to permit the fingers to spread apart as the barrel is pushed against the pole. The tapered end surfaces act as guides to direct the I.V. pole into the circular gripping portion. As the I.V. pole passes into the circular area the detents snap back into normal position and hold the I.V. pole tightly in the circular portion, which is preferably of slightly smaller diameter than the I.V. pole so as to grip it tightly and not slide up and down.

The barrel is closed at the bottom end by the lower end cap 18, which is constructed similarly to the upper end cap. The lower end cap has a flat circular plate portion 48 with a peripheral upstanding flange 50 of the appropriate size to fit snugly inside the barrel. The caps may be attached to the barrel by solvent, sonic welding or the like. The bottom cap has a center port 52 extending through the circular plate portion and an upstanding central circular flange 54 surrounding the center port for receiving the lower end of the manometer tube 12.

Like the upper cap, the lower end cap has a pair of fingers 22 integrally formed with the cap and extending outwardly therefrom. The fingers are generally parallel and lie substantially in the plane of the center plate portion of the lower end cap. The fingers are spaced sufficiently apart for receiving a standard or pole. Each finger has a tapered end surface 56 intercepted by a curved surface 58 to form a detent 60 on the facing surface of each finger. As noted earlier, the distance between the facing detents is determined to be less than the diameter of the standard or pole to which the pressure regulator is attached. The plastic from which the preferred cap is constructed, ABS resin, is sufficiently flexible that the fingers may be forced apart when pushed against the standard but snap back after the standard has passed the detents so as to hold the pressure regulator in a frictional gripping engagement with the standard and prevent it from sliding up and down. The caps are mounted on the barrel so that the fingers of each extend in the same direction and, when the barrel is mounted to a vertical standard, such as an I.V. pole, the pole will be held between the fingers of upper and lower caps.

For draining the barrel of any fluid accumulating between the manometer tube and the inside of the barrel, a drainage opening or port 62 is provided in the lower end cap 18 between the center flange 54 and the peripheral flange 50. A short extention or nipple 64, through which the drainage port 62 passes, extends downwardly from the plate portion 48 of the lower end cap.

To control drainage through the drain port 62, a plastic petcock, generally at 66, is mounted on the end of the nipple 64. The petcock has a body portion 68 with a center bore (not shown) and a tapered valve member 70 mounted in the body and having a passageway which is movable into and out of communication with the bore in the petcock body, thereby opening and closing the valve. The tapered valve member 70 may include an integral handle 72 for rotating the valve member, and is held in the body by a deformed flange 74 on the opposite side of the body from the handle. Preferably, the plastic to plastic contact between the valve member and the valve body are sufficiently close to prevent the ingress of bacteria or other microorganisms when the valve is closed.

The manometer tube 12 is mounted between the end caps 16 and 18 of the barrel 14. The manometer is preferably of hollow cylindrical plastic construction and graduated for easy reading. The lower end of the manometer is tapered for wedging tightly into the center flange 54 in the lower cap. The simple wedging contact is believed sufficient to prevent leakage, but the manometer tube may also be solvent sealed into the center flange. The upper end of the manometer tube resides in the receiving slot formed by the center depending flange 34 in the top cap 16. It may be freely inserted into the slot or held in the slot by adhesive. In any event, it is preferred that at least sufficient space be provided for venting through the end of the manometer tube into the chamber. With the manometer thus mounted between center flanges in the end caps, it is in a generally parallel and concentric relationship with the surrounding barrel, and the axes of the barrel and the manometer tube are colinear.

For providing an upper limit to the pressure of the selected body fluid, at least one and preferably two openings 20 are provided in the manometer tube, at a selected location above the lower end of the tube and within the chamber 13. The openings are positioned in the manometer tube corresponding to the desired maximum pressure of the body fluid. Thus, fluid reaching the openings cannot continue higher in the manometer tube but overflows through the openings to the space between the manometer tube and the barrel. This sets a maximum or upper limit to the pressure which will be attained by the body fluid. In the illustrated embodiment, two openings are at the same level but on opposite sides on the manometer tube.

When manufactured in sterile conditions, for one-time use only, it may be preferred to have a selection of pressure indicator and regulators available with the openings 20 at different locations, analogous to a glove available in various sizes. With such a selection, the doctor need only select the unit having the predetermined maximum pressure setting desired. For intracranial pressure regulators used with patients suffering from various brain traumas, it has been found that a limiting opening at about 28 cm above the lower end of the manometer tube has worked satisfactorily.

As indicated earlier, however, fluid flowing from the openings 20 normally reaches the bottom of the chamber by flowing down the side of the manometer tube. This liquid flow path leaves a residue adhering to the side of the manometer tube which provides a direct path for the migration of bacteria or other microorganisms into the column of fluid in the manometer, which runs directly from the patient. To isolate bacteria or microorganisms from the column of body fluid within the manometer tube, the drip platform or umbrella 26 is mounted around the manometer tube just below the openings 20. The drip platform extends outwardly from the manometer tube but does not touch the inside surface of the barrel 14. Fluid overflowing through the openings 20 cannot continue down the manometer tube, but is conducted to the peripheral edge of the drip platform, from which it drips or flows directly into the bottom of the chamber, free of any contact with the sides of the manometer tube between the collected liquid in the bottom of the barrel and the drip platform.

As seen more fully in FIG. 3, the drip platform 26 has a center cylindrical slip-ring 76 with a flat platform 78 formed therewith and extending radially outwardly from the manometer tube. The drip platform is preferably of one-piece plastic, e.g., ABS resin, construction. The slip-ring 76 is sized for a very snug fit along the manometer tube and solvent may be used to provide an extra-tight seal between the drip platform and the manometer tube. The underside of the peripheral edge of the platform has a tapered depending flange 80 which converges downwardly at an acute angle to provide for drop formation and to prevent liquid from flowing along the underside of the platform, other shapes or surface angles may be used. For example, the flat platform surface 78 may be at an obtuse angle, of greater than 90° but less than 180°, with the manometer rather than a right angle as shown in FIG. 3, or it may be curved like an umbrella canopy to conduct fluid downwardly therealong to drip off the peripheral edge. Any of these constructions may be used so long as they conduct the escaping fluid outwardly and permit it to drip or flow into the bottom of the chamber free of contact with the side walls of the manometer tube between the bottom of the chamber and the drip platform.

To convey the body fluid to the manometer 12, flexible plastic tubing 82 extends from the underside of the center port 52 in the lower end cap 18 to a catheter 84 which is inserted into the cavity containing body fluid. The plastic tubing is solvent sealed to the surface of the port 52 and is of sufficient length so that the barrel may be mounted on a vertical standard which need not be located immediately adjacent to the patient.

The particular type of catheter used may vary depending upon the body fluid being monitored, and the cavity in which it is placed. The tubing may terminate with a "Luer" type plug 86 for insertion into the selected of a variety of catheters. For sampling the body fluid or for injecting medicine, an access port 88 is provided into the tubing intermediate of the bottom cap and the catheter 84. The access port may be of ordinary Y-type construction but is preferably constructed in the manner described in pending U.S. Application Ser. No. 706,363, filed July 9, 1976, now U.S. Pat. No. 4,048,995, the contents of which are incorporated by referenced herein.

It can be seen from the description above that in accordance with the present invention a fluid pressure indicator and regulator may be quickly and simply mounted to a vertical standard, such as an I.V. pole, which is readily available at all hospitals. For providing a barrier to the possible contamination of body fluid residing in the manometer tube, a drip platform is provided below the pressure limiting openings to cause escaping fluid to flow into the chamber without contacting the sides of the manometer tube. Thus, there is not a continuous liquid path along the manometer tube for any harmful microorganisms or bacteria to migrate to the openings and into the fluid which communicates directly with the patient. Although this invention has been described in terms of the preferred embodiment, it is also intended to cover any changes or variations which may be made and which come within the following claims.

That which is claimed is:

1. In a body fluid measuring device comprising a chamber, an elongated indicator tube carried at least in part within said chamber, conduit means in flow communication with one end of said tube for conveying body fluid thereto, the distance of travel of fluid along said tube representing the pressure of the body fluid and at least one opening means in said indicator tube through which body fluid may flow into said chamber, the improvement comprising overflow control means including an annular platform carried by said indicator tube below said opening means to conduct overflowing fluid outwardly from said indicator tube and permit it to drop from the peripheral edge of said platform into said chamber generally free of contact with the indicator tube.

2. A body fluid measuring device in accordance with claim 1 wherein said peripheral edge includes drop forming means to prevent liquid from flowing beneath said platform to contact said indicator tube.

3. A body fluid measuring device in accordance with claim 1 wherein said platform extends generally radially from said indicator tube at an angle greater than or equal to 90° and less than 180°.

4. A body fluid measuring device in accordance with claim 1 wherein said chamber is defined by an elongated barrel closed at each end by integral caps, each cap including integral snap-on attachment fingers for mounting said barrel to a vertical standard.

* * * * *